US00PP12862P2

(12) United States Plant Patent
Pouw

(10) Patent No.: US PP12,862 P2
(45) Date of Patent: Aug. 20, 2002

(54) MINIATURE ROSE PLANT NAMED 'RUIKENRE'

(75) Inventor: Antonius A. Pouw, De Kwakel (NL)

(73) Assignee: De Ruiter's Nieuwe Rozen, B.V., De Kwakel (NL)

( * ) Notice: Subject to any disclaimer, the term of this patent is extended or adjusted under 35 U.S.C. 154(b) by 0 days.

(21) Appl. No.: 09/665,261

(22) Filed: Sep. 19, 2000

(51) Int. Cl.[7] ..... A01H 5/00
(52) U.S. Cl. ..... Plt./122
(58) Field of Search ..... Plt./122, 116

(56) References Cited

PUBLICATIONS

UPOV–ROM GTITM Computer Database 2001/03, Jun. 21, 2001, GTI Jouve Retrieval Software, Citation for Rosa 'Ruikenre'.*

* cited by examiner

*Primary Examiner*—Bruce R. Campell
*Assistant Examiner*—June Hwu
(74) *Attorney, Agent, or Firm*—C. A. Whealy

(57) ABSTRACT

A distinctive cultivar of miniature rose plant named 'Ruikenre', characterized by its glossy dark green leaves; dense and bushy growth habit; large double red-colored flowers arranged in tight sprays; strong rooting habit; and excellent postproduction longevity.

2 Drawing Sheets

BACKGROUND OF THE INVENTION

The present invention relates to a new and distinct cultivar of the miniature rose class, botanically known as *Rosa hybrida*, and hereinafter referred to by the cultivar name Ruikenre.

The new cultivar is a product of a planned breeding program conducted by the Inventor in Hazerswoude, The Netherlands. The objective of the breeding program was to develop new pot rose varieties with novel and attractive flower colors and excellent postproduction longevity.

The new cultivar originated from a cross made by the Inventor of two unnamed proprietary seedling selections. The cultivar Ruikenre was discovered and selected by the Inventor as a flowering plant within the progeny of the stated cross in a controlled environment in Hazerswoude, The Netherlands, in 1995.

Asexual reproduction of the new cultivar by cuttings taken at Hazerswoude, The Netherlands, has shown that the unique features of this new miniature rose plant are stable and reproduced true to type in successive generations of asexual reproduction.

SUMMARY OF THE INVENTION

The following traits have been repeatedly observed and are determined to be the unique characteristics of 'Ruikenre'. These characteristics in combination distinguish the new miniature rose plant as a new and distinct cultivar:

1. Dark green glossy leaves.
2. Dense and bushy growth habit.
3. Large double red-colored flowers arranged in tight sprays.
4. Strong rooting habit.
5. Excellent postproduction longevity.

Plants of the new miniature rose plant can be compared to plants of the cultivar Ruikalla, disclosed in U.S. Plant Pat. No. 9,634. In side-by-side comparisons conducted by the Inventor in De Kwakel, The Netherlands, plants of the new miniature rose plant are larger and bushier than plants of the cultivar Ruikalla. In addition, flowers of plants of the new miniature rose are larger and more intense red in color than flowers of plants of the cultivar Ruikalla.

Plants of the new miniature rose plant can also be compared to plants of the cultivar Ruijef, disclosed in U.S. Plant Pat. No. 9,635. In side-by-side comparisons conducted by the Inventor in De Kwakel, The Netherlands, plants of the new miniature rose plant are more compact and more freely flowering than plants of the cultivar Ruikalla. In addition, flowers of plants of the new miniature rose are larger and lighter red in color than flowers of plants of the cultivar Ruijef.

The new miniature rose plant has not been observed under all possible environmental conditions. The phenotype may vary significantly with variations in environment such as temperature and light level, without, however, any variance in genotype.

BRIEF DESCRIPTION OF PHOTOGRAPHS

The accompanying colored photographs illustrate typical plants of the new miniature rose plant, showing the colors as true as it is reasonably possible to obtain in colored reproductions of this type. Colors in the photographs may differ slightly from the color values cited in the detailed botanical description which more accurately describe the actual colors of the new minature rose.

The photograph at the top of the first sheet comprises a top perspective view of a typical 12.5-cm container of 3- month-old plants of 'Ruikenre' grown in Salinas, Calif.

The photograph at the bottom of the first sheet is a close-up view of a typical flowering plant of 'Ruikenre'.

The photograph on the second page is a close-up view of upper and lower surfaces of typical three and five-leaflet leaves and typical developing flowers of 'Ruikenre'.

DETAILED BOTANICAL DESCRIPTION

The following observations and measurements describe plants grown in Salinas, Calif., in fiberglass-covered greenhouses under conditions which closely approximate commercial production conditions during the spring. Plants were about 3-months old and were grown in 12.5-cm containers. In the following description, color references are made to The Royal Horticultural Society Colour Chart except where general terms of ordinary dictionary significance are used.

Classification:

*Botanical.*—*Rosa hybrida* cultivar Ruikenre.

*Commercial.*—Miniature pot rose.

Parentage:

*Female and male parents.*—Unnamed proprietary seedling selections of *Rosa hybrida.*

Propagation:

*Type.*—Terminal or stem cuttings.

*Time to rooting.*—About 8 to 10 days at soil temperatures of 20° C.

*Rooting habit and description.*—Propagates easily; roots strong, vigorous and well-branched.

Plant description:

*Form.*—Upright and outwardly spreading; uniform plant habit; dense and bushy.

*Plant height.*—About 28 cm.

*Plant width.*—About 30 cm.

*Growth habit.*—Vigorous; suitable for 10-cm and larger containers.

*Crop time.*—Time to produce a finished plant in a 10-cm container about 25 cm in height and about 25 cm in width is generally about 10 to 12 weeks depending on day and night temperatures, light level, and cultural practices.

*Stem and lateral branches.*—Branching habit: Freely branching; lateral branches typically form at every node when plants are pinched. Generally plants are pinched to increase lateral branching. Branches flexible, but very strong. Diameter of lateral branches, base: About 4.5 mm. Internode length: About 1.5 cm. Texture: Smooth. Color: 146A or slightly darker. Thorns: Amount: Few to scarce; random. Height: About 3 mm. Diameter at base: About 2.5 mm. Shape: Linear. Color: Close to 146A.

*Foliage description.*—Leaves arranged alternately, compound with typically three to seven leaflets per leaf, generally symmetrical, abundant, and flat in aspect. Stipules at petiole base; stipules about 7.5 mm in length, linear, and similar to the leaf in color. Leaf length, seven-leaflet leaves: About 7.6 cm. Leaf width, seven-leaflet leaves: About 4.1 cm. Terminal leaflet length: About 2.7 cm. Terminal leaflet width: About 1.8 cm. Leaflet shape: Ovate. Leaflet apex: Acute. Leaflet base: Obtuse. Leaflet margin: Serrate. Leaflet texture: Smooth; upper surface, glossy; lower surface, dull. Petiole length: About 1.3 cm. Rachis length: About 2.9 cm. Petiole diameter: About 1 mm. Color: Young foliage, upper surface: Close to 147A with dark red, close to 187A, undertones; narrow dark red, close to 187A, margins. Young foliage, lower surface: Close to 148A with dark red, close to 187A, undertones. Mature foliage, upper surface: Close to 147A; narrow dark red, 187A, margins. Mature foliage, lower surface: Close to 148B with dark red, close to 187A, undertones. Petiole/rachis, upper surface: 146A with dark red, close to 187A, undertones. Petiole/rachis, lower surface: 146A.

Flower description:

*Flower type and habit.*—Large double red flowers. Consistently symmetrical rosette flowers that are mostly hemispherical in shape. Freely and continuously flowering. Flowers arranged in tight terminal sprays with usually about three or four flowers per spray. Flowers persistent.

*Flowering season.*—Year-round under greenhouse conditions; in the garden, optimal flowering occurs from spring through autumn.

*Flower diameter.*—About 4.1 cm.

*Flower depth* (*height*).—About 2.1 cm.

*Flower longevity on plant.*—About 12 to 14 days.

*Postproduction longevity.*—More than three weeks under interior conditions.

*Fragrance.*—Faint, typical of Rosa.

*Flower buds* (*before stage of showing color*).—Shape: Ovoid. Length: About 2.2 cm. Diameter: About 9 mm. Color: 144A, with dark red, close to 187A, random trichomes.

*Petals.*—Quantity: About 35 per flower arranged in about seven rows. Length, outer petals: About 2.1 cm. Width, outer petals: About 1.9 cm. Shape: Fan-shaped to ovate. Apex: Rounded. Base: Attenuate. Margin: Entire. Texture: Smooth, velvety. Color: When opening, upper surface: 45A; base, white, 155D. When opening, lower surface: 45B; base, white, 155D. Fully opened, upper surface: 45A, fading to 45B with subsequent development; base, white, 155D. Fully opened, lower surface: 45C; base, white, 155D.

*Sepals.*—Quantity: Five. Length: About 1.6 cm. Diameter: About 1 cm. Shape: Elongate to narrowly ovate, occasionally with foliaceous appendages. Apex: Sharply pointed. Base: Obtuse. Texture: Upper surface, fine white hairs; lower surface, dark red, close to 187A, trichomes. Color: Upper surface: 144A to 144B; covered with fine white hairs. Lower surface: 144A.

*Peduncles.*—Strength: Good yet flexible. Aspect: About 30 to 45° from vertical. Length: About 2.3 cm. Diameter: About 2.5 mm. Texture: Glabrous. Color: 144A.

*Reproductive organs.*—Stamens: Quantity: About 30 per flower. Anther size: About 1.5 by 1 mm. Anther shape: Bi-lobed. Anther color: Close to 3D. Pollen: None. Pistils: Quantity: About 10 per flower. Style length: About 3.2 mm. Style color: Close to 59A; translucent.

*Seed.*—Seed production has not been observed.

*Hips.*—Hip production has not been observed.

Disease/pest resistance: Plants of the new miniature rose have not been shown to be reistant to known pathogens and pests common to miniature roses.

Temperature tolerance: Plants of the new miniature rose have been observed to be tolerant to temperatures from 0 to 45° C.

It is claimed:

1. A new and distinct miniature rose plant named 'Ruikenre', as illustrated and described.

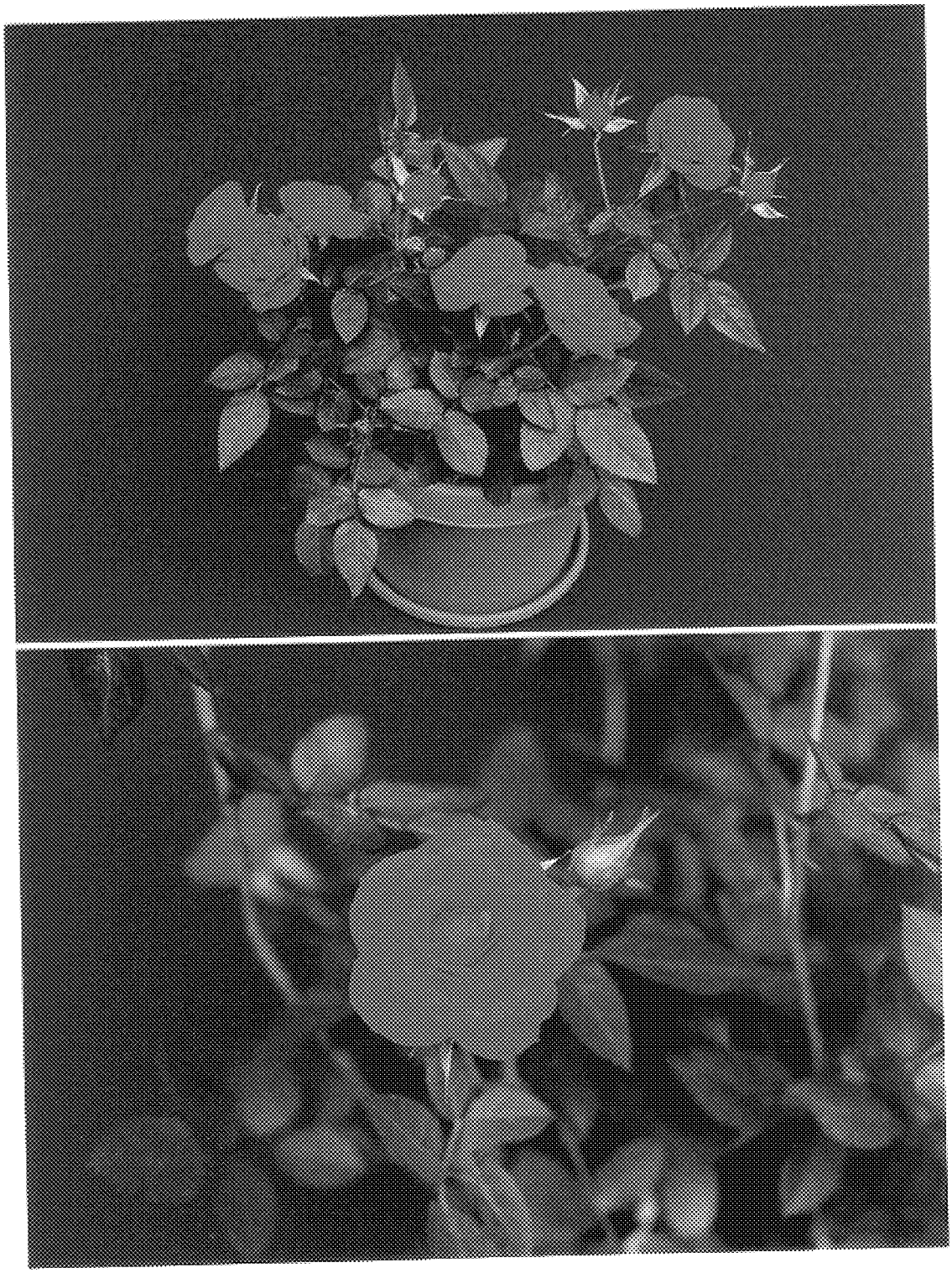

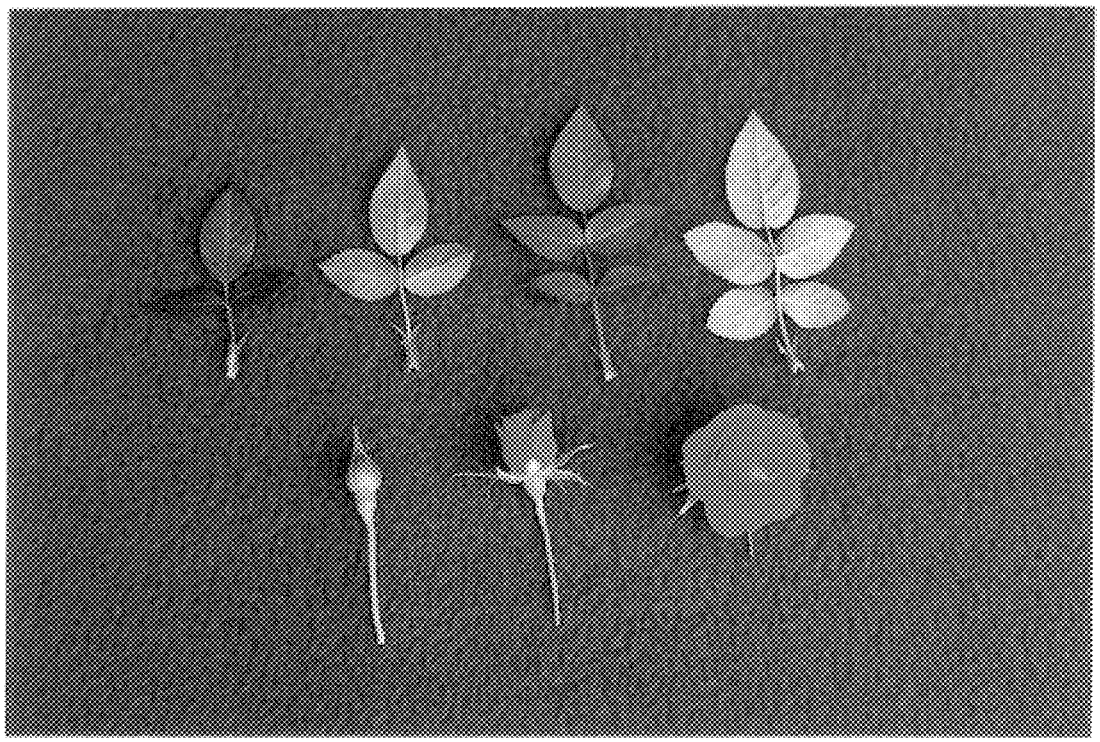

* * * * *